United States Patent [19]

Angel et al.

[11] Patent Number: 4,781,458
[45] Date of Patent: Nov. 1, 1988

[54] FIBER OPTIC APPARATUS FOR DETECTING MOLECULAR SPECIES BY SURFACE ENHANCED RAMAN SPECTROSCOPY

[75] Inventors: Stanley M. Angel, Livermore, Calif.; Shiv K. Sharma, Honolulu, Hi.

[73] Assignee: The United States of America as represented by the United States Department of Energy, Washington, D.C.

[21] Appl. No.: 126,159

[22] Filed: Nov. 30, 1987

[51] Int. Cl.[4] ............................................. G01N 21/65
[52] U.S. Cl. ................................................... 356/301
[58] Field of Search ......................... 356/301, 317, 318

[56] References Cited

U.S. PATENT DOCUMENTS 4,674,878   6/1987   Vo-Dinh ............................. 356/301

*Primary Examiner*—Vincent P. McGraw
*Attorney, Agent, or Firm*—Michael B. Lee; L. E. Carnahan; Judson R. Hightower

[57] ABSTRACT

Optrode apparatus for detecting constituents of a fluid medium includes an optical fiber (13, 13a to 13e) having a metal coating (22, 22a to 22e) on at least a portion of a light transmissive core (17, 17a to 17d). The metal is one, such as silver, gold or copper, which enhances emission of Raman signal frequencies by molecules adsorbed on the surface of the coating when monochromatic probe light of a different frequency is scattered by such molecules and the metal coating is sufficiently thin to transmit light between the absorbed molecules and the core of the fiber. Probe light is directed into one end of the fiber and a detector (16, 16d, 16e) analyzes light emitted from the fiber for Raman frequencies that identify one or more particular molecular species. In one form, the optrode (13e) may function as a working electrode of an electrochemical cell (53) while also serving to detect the products of oxidation or reduction reactions which occur at the electrode surface.

23 Claims, 3 Drawing Sheets

FIBER OPTIC APPARATUS FOR DETECTING MOLECULAR SPECIES BY SURFACE ENHANCED RAMAN SPECTROSCOPY

The United States Government has rights in this invention pursuant to Contract No. W-7405-ENG-48 between the United States Department of Energy and the University of California for operation of the Lawrence Livermore National Laboratory.

TECHNICAL FIELD

This invention relates to apparatus for detecting one or more chemical compounds within a liquid medium. More particularly the invention relates to fiber optical apparatus for sensing the presence of one or more molecular species by detection of Raman frequency shifts in light which has been scattered by the species.

BACKGROUND OF THE INVENTION

Raman spectroscopy is a proven and effective technique for qualitatively or quantitatively detecting specific chemical compounds within a liquid medium. Monochromatic probe light of a known frequency or wavelength is directed into the liquid. A portion of the probe light photons momentarily change the energy states of individual molecules within the liquid. The excited molecules then emit Raman signal photons which have frequencies that differ from that of the probe light by amounts which characterize and identify the particular molecular species. Thus the presence of one or more molecular species can be detected and quantified if desired by analyzing the scattered probe light for the characteristic Raman signals of such species.

Raman signals can be very weak making detection difficult. Surface enhanced Raman spectroscopy is a known technique for increasing Raman signal emission. In particular, it has been found that constituents of a liquid which are adsorbed on the surface of certain metals, such as silver, gold or platinum, exhibit greatly increased Raman signal emission by factors of up to $10^6$ in some cases.

Prior apparatus for practicing suface enhanced Raman spectroscopy has tended to be undesirably complex, bulky and costly and is also subject to operational limitations. Under some conditions, the Raman signals of interest are diluted or masked by fluorescence originating in portions of the liquid that are away from the metal adsorbtion surface. Conventional apparatus does not localize the analysis to Raman emissions from molecules adsorbed on the metal surface at least to a desirable extent. In investigating reactions in an electrochemical cell, for example, it may be desirable to obtain signals only from the immediate region of an electrode where initial reduction or oxidation reactions occur. The composition of the cell fluid away from the electrode may be distinctly different due to subsequent reverse reactions.

The prior role of optical fibers in surface enhanced Raman spectroscopy has been the limited one of transmitting probe light into the liquid medium and/or returning scattered light for frequency analysis. probe light is directed into one end of the fiber and the other end is spaced from the metal surface in position to direct the probe light to substances adsorbed on the surface and/or to receive light which has been scattered by such substances. This does not resolve the above discussed deficiencies of the conventional apparatus at least to the desirable extent.

The present invention is directed to overcoming one or more of the problems discussed above.

SUMMARY OF THE INVENTION

In one aspect of the present invention, apparatus for detecting one or more molecular species in a liquid medium by surface enhanced Raman spectroscopy includes at least one optical fiber having a light transmissive core and having a coating of metal on at least a portion of the core. The metal coating is sufficiently thin to transmit light and the metal is one which enhances emission of Raman signals by substances adsorbed on the surface of the coating. The apparatus further includes light source means for directing probe light into the optical fiber and detector means for detecting Raman signals in light which is emitted by the optical fiber.

In another aspect of the the invention, apparatus for detecting one or more substances in a fluid medium includes an optical fiber with first and second opposite ends and which has a light transmissive core and a coating of metal on the side surface of the core at least in the region of the first end. The metal of the coating is one which enhances emission of Raman signal by substances adsorbed on the surface of the coating and the coating is sufficiently thin to enable light transmission between the core and such substances. The apparatus also includes a monochromatic probe light source, detector means for detecting specific frequencies of light and means for directing the probe light into the second end of the fiber and for directing light which is emitted from the optical fiber to the detector means.

In still another aspect, the invention provides an optical fiber probe for use in detecting one or more constituents of a fluid, the probe having a light transmissive core and a metallic coating on at least a portion of the core. The metal of the coating is of a type which enhances emission of Raman signal light by substances adsorbed on surface of the coating and the coating is sufficiently thin to transmit light between the core and such substances.

In another aspect of the invention, apparatus for detecting one or more molecular species in electrolytic liquid in an electrochemical cell also functions as an electrode of the cell. The apparatus includes at least one optical fiber having a light transmissive core and a metal coating on at least a portion of the core. The coating is sufficiently thin to enable light transmission bethe core and the outer surface of the coating and the metal is of a type which enhances emission of Raman signal frequencies by molecules adsorbed on the coating surface. The apparatus further includes means for directing probe light into an end of the fiber and means for detecting Raman signals in light which is emitted by the fiber. The fiber has an electrical contact region which includes a layer of electrically conductive metal on a portion of the core which layer is in electrical contact with the coating and which is thicker than the coating whereby an electrical conductor may be connected to the thin coating.

The invention provides apparatus for detecting molecular species within a liquid medium by Raman spectroscopy which is structurally simplified and which can be very compact and economical. The metallic enhancement surface is an integral component of the optical fiber probe itself. Raman signals from substances adsorbed on the metal coating enter the fiber directly, without passage through the bulk of the liquid medium, as the coating is sufficiently thin to be light transmissive. The optical fiber probe can be configured, when necessary, to present only light which originates at the metal surface of the probe to the Raman signal detector. Fluorescence from the bulk liquid can be excluded from the light which is returned to the detector. The optical fiber probe can, without complications, transmit Raman signals for very long distances when necessary. In one form of the invention, the optical fiber can operate as an electrode in an electrochemical cell while also enabling detection of reactions which occur at the surface of an electrochemical cell electrode.

DETAILED DESCRIPTION OF THE PREFERRED EMBODIMENTS

Figure 1:
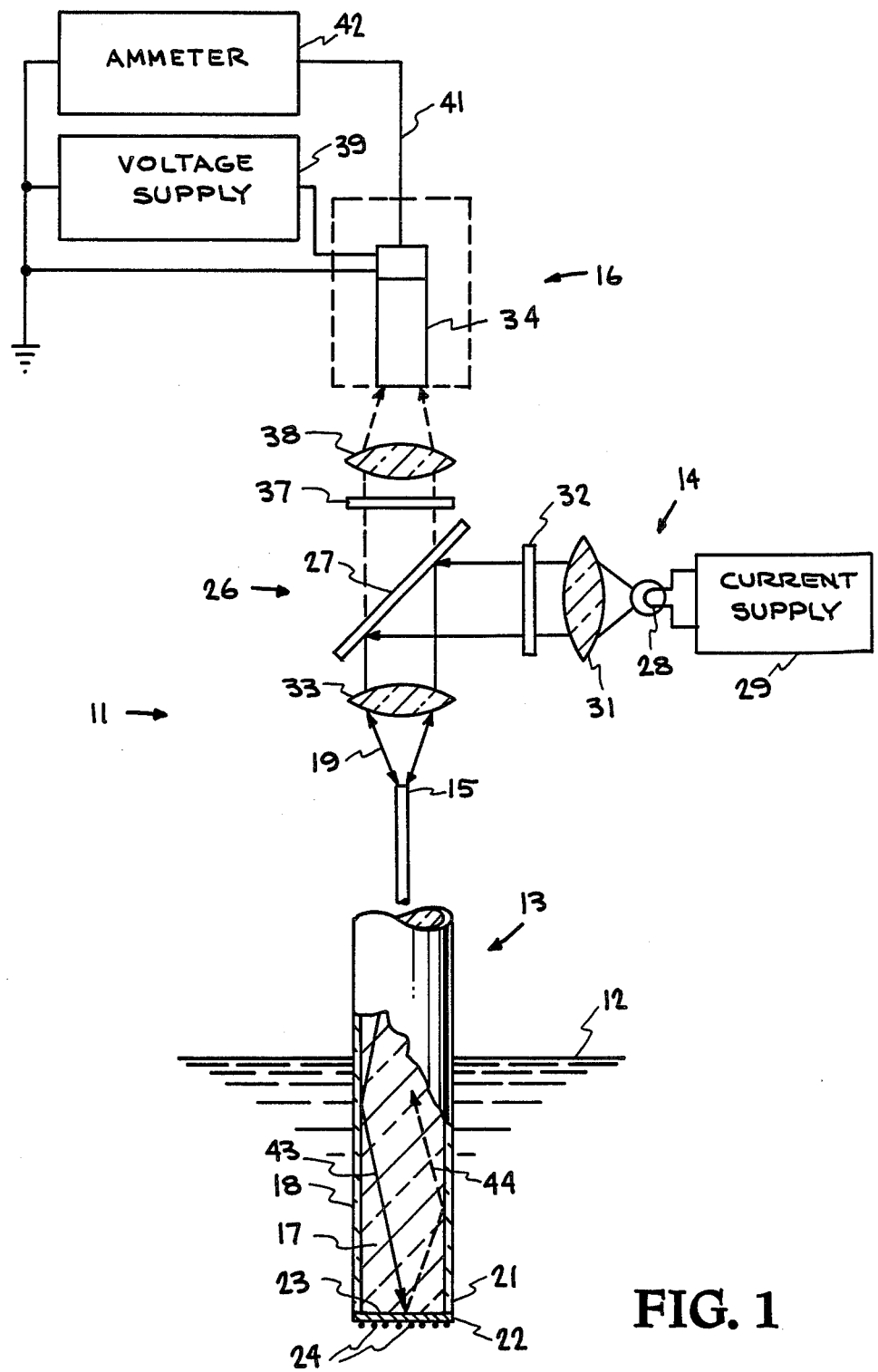
FIG. 1 is a partially schematic view of fiber optic apparatus for detecting one or more constituents of a liquid by surface enhanced Raman spectoscopy in accordance with one embodiment of the invention.

Referring initially to FIG. 1 of the drawings, apparatus 11 for detecting one or more constituents of a liquid medium 12 includes an optrode or optical fiber probe 13 which may be extended into the liquid medium, light source means 14 for directing probe light into one end 15 of the optical fiber and detector means 16 for detecting Raman signals in light which is emitted from the fiber.

The optical fiber 13 of this embodiment has a light transmissive core 17 formed of high index of refraction glass or similar material and has a cladding 18 of relatively low index of refraction glass or the like on the side surface of the core. In many cases optical fibers 13 of this general type are very thin in relation to their length and may have diameters ranging down to 100 microns or less although relatively thick fibers may be used in some embodiments of the present apparatus 11 in order to provide a larger area of contact with the liquid medium 12.

Light that is directed into an end 15 of the optical fiber 13 along ray paths 19 lying within the acceptance angle of the fiber propagates to the other end 21 of the fiber by undergoing repetitive total internal reflections at the interface between core 17 and cladding 18 in a manner well understood within the art.

The optical fiber 13 of this embodiment has a thin coating 22 of metal on the end surface 23 at end 21, the metal being one of the types which enhances emission of Raman signal light by molecules 24 of the liquid 12 that are adsorbed on the surface of the metal when incident probe light of different wavelength is scattered by such molecules. Silver, gold or cooper are the preferred metals for the purpose as such metals exhibit a very strong degree of enhancement.

Metal coating 22 is sufficiently thin that it is light transmissive. To enable light transmission between core 17 and molecules 24 adsorbed on the outer surface of the coating 22, the coating thickness is preferably in the range from about 10 to about 50 Angstrom units although thicknesses outside that range may be suitable under some conditions. Coatings 22 of one of the above described metals may be formed with thicknesses in that range by vacuum deposition, for example. It has been the general practice to roughen metal surfaces that are to be used for surface enhancement of Raman signal emission as this increases the enhancement effect. Such rougening is not needed, at least in many cases, in the present apparatus as the metal of such extremely thin coatings 22 tends to form into microclusters on the glass surface and thus the coating is inherently roughened.

Means 26 are provided for directing probe light from light source 14 into end 15 of the optical fiber 13 and for directing light which is emitted from that end of the fiber to the detector means 16. In the present example of the invention, such means 26 includes a dichroic mirror 27 of the known type which reflects light having frequencies within a specific narrow band and which transmits light of other frequencies. Mirror 27 is Spaced from end 15 of optical fiber 13 and oriented at a 45° angle with respect to the optical axis of the end of the fiber.

The probe light source 14 of this embodiment includes an electrical lamp 28 operated from a regulated current supply 29 and a lens 31 positioned to direct light from the lamp to mirror 27 along a light path which is at right angles to the optical axis of end 15 of the fiber 13. A color filter 32 situated between lens 31 and mirror 27 transmits only a narrow band of frequencies that is within the range of frequencies that is reflectable by the dichroic mirror. Thus the probe light source 14 is essentially monochromatic.

Another lens 33, between mirror 27 and optical fiber 13, focusses the probe light that is reflected by mirror 27 into the end 15 of the fiber.

Lamp 28 may be replaced with a laser in instances where a more intense input of probe light is needed or where probe light of a single wavelength is desired. An adjustable wavelength light source may also be used to enable selection of any of a number of different probe light frequencies. Dichroic mirror 27 may in some cases be replaced with a half silvered mirror of the type which reflects a portion of incident light while transmitting another portion although such a mirror delivers less of the output of light source 14 to the fiber 13 and less of the Raman signal light to detector 16.

The term "light" as used herein and in the appended claims should be understood to refer to the portion of the electromagnetic spectrum that ranges from far ultraviolet to far infrared rather than to just the visible light band. Both the probe light and the Raman signals may in some cases be outside the visible band of the spectrum.

Detector means 16 is positioned to receive light which is emitted from end 15 of fiber 13 and transmitted through lens 33 and dichroic mirror 27. The detector means 16 may be any of the variety of devices which analyze light on the basis of frequency and which indicate the presence of one or more specific frequencies. Very high sensitivity to weak Raman signals is provided for in the embodiment by using a photomuplier tube 34 which is preferably cooled. A color filter 37 of the type which transmits only a specific predetermined narrow band of frequencies is disposed between the photomultiplier tube 24 and mirror 27. A lens 38 may be situated between filter 37 and tube 34 to focus light from the mirror 27 onto the light sensitive area of the tube in instances where that area has a diameter smaller than that of the light path through the filter.

Photomultiplier tube 34 receives operating voltage from a voltage supply 39 and the signal output conductor 41 of the tube is connected to ground through a current indicator 42 which may be an ammeter of either the digital or analog type.

The apparatus of FIG. 1 may be used to detect various specific molecules in any of a variety of liquid mediums 12. As one example, which should not be considered to be limitative, the apparatus may be used to monitor ground water for organic contaminants such as pesticides or herbicides.

In the operation of the embodiment of FIG. 1, end 21 of the optical fiber 13 is immersed in the fluid medium 12 causing molecules 24 of the fluid constituents to adsorb on the surface of the metal coating 22. Light source 14 is then actuated causing mirror 27 and lens 33 to direct probe light of a particular frequency into end 15 of optical fiber 13. The probe light propagates along the fiber 13 primarily by repeated total internal reflections at the interface between core 17 and cladding 18 although some light may travel directly through the fiber if it is linear.

Upon reaching the end surface 23 of fiber 13, probe light 43 passes through the extremely thin metal coating 22 and is scattered by the molecules 24 which are adsorbed on the coating surface. This causes changes in the energy states of such molecules 24 which result in emissions of Raman signal frequencies that differ from the frequency of the probe light 43. Different chemical species of molecules 24 produce Raman signals 44 having frequencies that differ from the frequency of the probe light 43 by different amounts. The characteritic Raman frequency shifts produced by particular molecular species 24 are known or can be ascertained by optical probing of a pure sample. Thus the presence of One or more particular species 24 can be determined by analyzing the Raman signal light 44 for the frequencies that characterise the particular species. The intensity of such frequencies indicates the abundance of the particular species in the fluid 12 at the surface of coating 22.

A portion of the Raman signal emission 44 from molecules 24 enters the optical fiber 13 and propagates to the opposite end where it is emitted and transmitted on to the detector means 16 through lens 33, mirror 27, filter 37 and lens 38. The filter 37 is a selected one which transmits only a Raman signal frequency that characterizes the particular molecular species 24 that is to be detected. A series of different filters 37 may be used in instances where it is necessary to identify more than one frequency in order to distinguish a particular molecular species from others or where it is desired to detect a number of species. Alternately, the filter 37 may be replaced with an adjustable monochromator of the known form which transmits a selected frequency.

Raman signals 44 which reach photomultiplier tube 34 result in an output current from the tube that is detected and indicated by the current detector 42. The magnitude of the output current is indicative of the abundance of the particular molecular species 24 in fluid 12 at least at the surface of metal coating 22.

The optrode 13 of the present invention is a highly efficient collector of Raman signals 44 as the metal surface which enhances emission of such signals is at the optical fiber itself.

Figures 2, 3, 4:
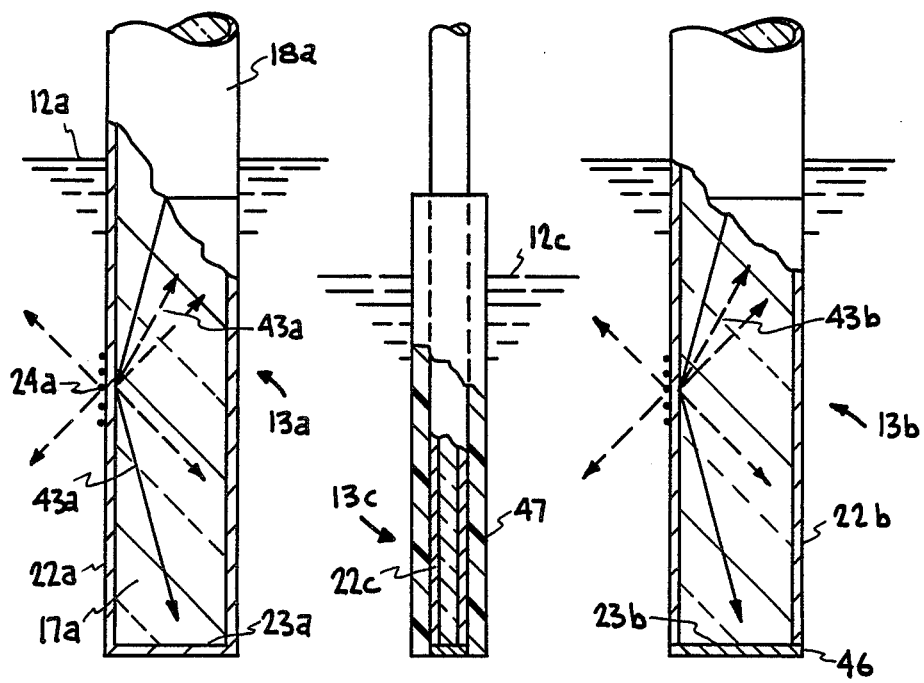
FIG. 2 is a broken out view of one end of a modified optrode or optical fiber probe which can be utilized in the apparatus of FIG. 1.
FIG. 3 is a broken out view of another modification of the optrode component of the apparatus.
FIG. 4 is a broken out view of a portion of still another modification of the optrode component.

While probe light 43a which propagates along the fiber 13 by total internal reflections is emitted from core 17 only at the end surface 23, such light does interact with a very thin layer of the material adjacent the core which material is cladding 18 in the embodiment of FIG. 1, the interaction being referred to in the art as the evanescent wave. Referring now to FIG. 2, this enables an extension of the area of the metal coating 22a to obtain a larger amount of Raman signals. In particular, the glass cladding 18a may be removed from at least a portion of the side surface of core 17a and replaced with additional thin metal coating 22a similar to that which has been previously described. Such coatings 22a are sufficiently thin to enable emission of Raman signals 43a by substances 24a adsorbed at the coating surface in response to the evanescent wave. A portion of such signals 43a enter the fiber 13a and are transmitted to the detector along with the Raman signals which enter end surface 23a.

Removal of the the glass cladding 18 from the side surface of core 17a for the above described purpose does not disrupt the operation of the fiber 13a with respect to propagating light by total internal reflections. Most liquids 12a into which the fiber 13a will be inserted have indices of refraction substantially lower than that of the core 17a and thus function in the manner of cladding although the maximum angle of total reflection may be reduced somewhat.

The optrode 13a need not necessarily be linear as depicted in FIG. 2 and may be coiled or otherwise convoluted in order to increase the area of metal coating 22a that is exposed to liquid 12a within a given volume of the liquid and thereby obtain stronger Raman signals.

Raman signals 43a originating at the portion of the coating 22a which is at the end surface 23a of fiber 13a may under some conditions be accompanied by fluorescence from the bulk liquid 12a that is away from the coating. Such fluorescence does not enter the fiber 13a through the portions of coating 22a at the sides of core 17a in a manner which enables propagation of such fluorescence along the fiber. External light arriving at low angles is reflected away by by the side surface of the fiber 13a. Light arriving at more perpendicular angles is refracted and emitted from the opposite side of the fiber 13a as it is not directed at an angle which enables propagation along the fiber by total internal reflections. Thus the only light that is transmitted to the detector from the side of core 17a is light which originates in the evanescent wave region immedadjacent core 17a. As a practical matter such light originates at least largely at the molecules 24a which are adsorbed on the coating 22a at the side region of the fiber 13a. In other words, data obtained through the sides of the fiber 13a is localized to the immediate region of the fiber.

The effect can be used to exclude fluorescence from the bulk of the liquid 12a from the signals which are transmitted to the detector which fluorescence can be very strong under some conditions and thereby mask Raman signals which may also be present. Referring now to FIG. 3, an optrode 13b for this purpose may be similar to that described with respect to FIG. 2 except that in the embodiment of FIG. 3 the metal coating 22b is not present on the end surface 23b. Instead, end surface 23b is covered with a layer 46 of opaque material. Thus all light 43b that is transmitted back to the detector is Raman signals and/or fluoresence that originates in a minutely thin region at the side of the fiber 13b.

If it is desired to detect Raman signals only from a particular molecular species or group of such species, the modification depicted in FIG. 4 may be utilized. In this embodiment, the metal coating 22c is itself covered with a layer 47 of material which is selectively absorbent of the species or group of species to be detected and which is non-absorbent of the other constituents of the liquid medium 12c. Polystyrene plastic, for example, is selectively absorbent of long chain hydrocarbons such as are found in gasoline or other petroleum derivatives.

Figure 5:
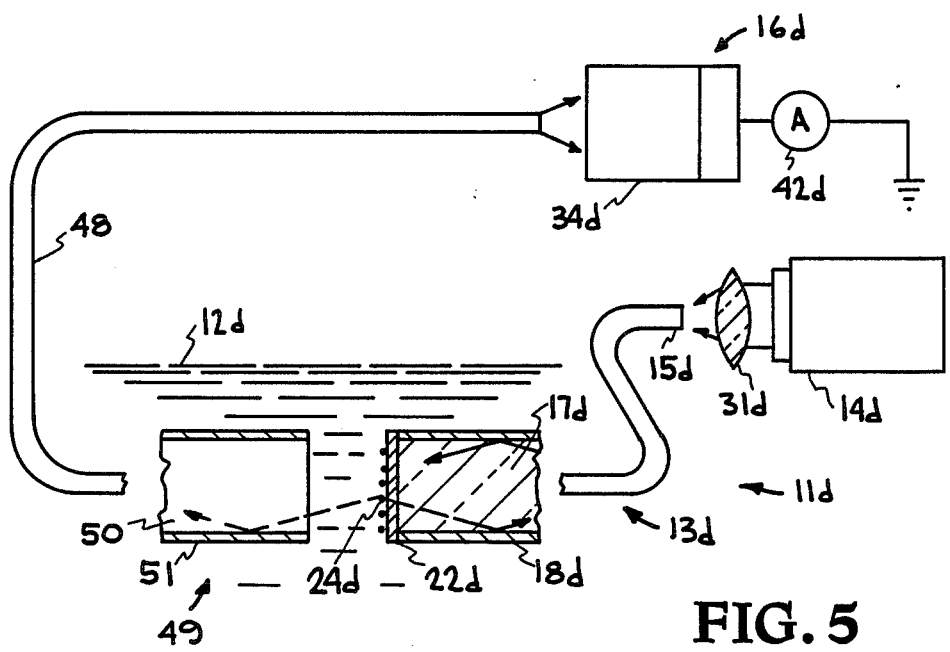
FIG. 5 is a diagramatic illustration of fiber optic apparatus for detecting one or more constituents of a liquid in accordance with another embodiment of the invention.

In the embodiments of the invention which have heretofore been described, the optical fiber 13c transmits probe light to the metal coating 22c and also returns Raman signals to the detector. The structural complications required for separating the two types of light can be avoided by the modification shown in FIG. 5. The optical fiber 13d of the embodiment of FIG. 5 may be similar to that previously described with reference to FIG. 1. Thus the fiber 13d of FIG. 5 has a light transmissive core 17d with glass cladding 18d and a thin metal coating 22d of the hereinbefore described type on the end surface 23d of the fiber. The light source 14d of this embodiment is aligned with the other end 15d of the fiber 13d and directs probe light into the fiber through a focussing lens 31d to induce Raman signals from substances 24d adsorbed on the surface of coating 22d.

Raman signals are intercepted and transmitted to the detector means 16d by an additional optical fiber 48 having an end immersed in the liquid medium 12d and facing metal coating 22d.

Figure 6:
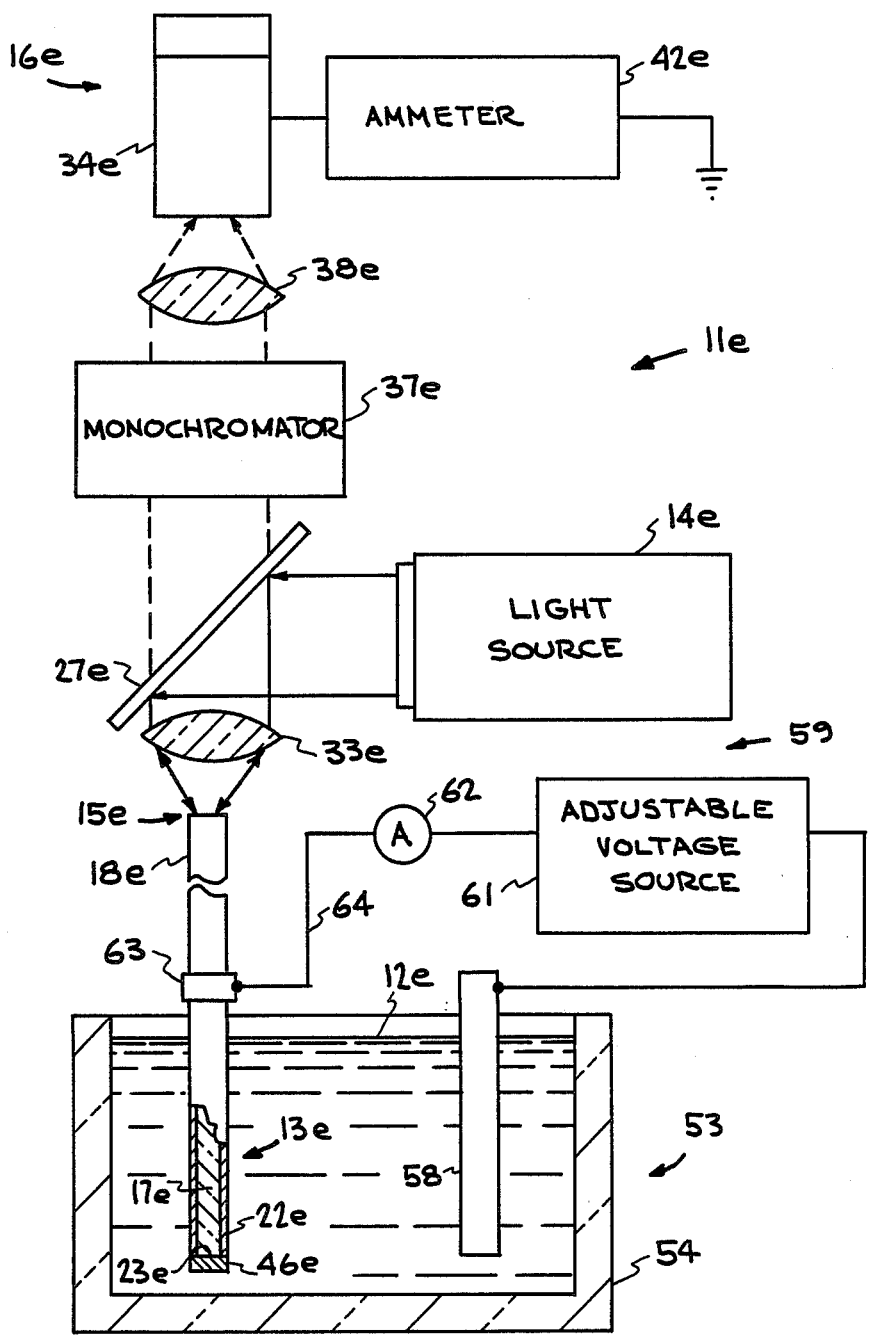
FIG. 6 is a partially schematic view of still another embodiment of the invention having an optrode which serves as an electrode of an electrochemical cell and which also enables detection of electrolytic fluid constituents at the surface of the electrode.

Referring now to FIG. 6, an optical fiber probe 13e embodying the present invention is uniquely adapted for studying or monitoring reactions which occur within an electrochemical cell 53 as the fiber may itself function as one of the electrodes of the cell. This enables the apparatus 11e to sense and quantitate molecular species that are generated in the electrolytic fluid 12e at the surface of an electrode. prior equipment for studying such reactions by Raman spectroscopy is more complex and does not enable the same degree of localization of the data to the immediate region of the electrode surface.

The electrochemical cell 53 may be of one of the known constructions aside from the presence of the optical fiber electrode 13e and the probe light source 14e and detector means 16e which are coupled to the fiber. Thus the cell 53 may have a vessel 54 containing the electrolytic fluid 12e, an additional electrode 58 extending into the fluid in spaced apart relationship with the fiber electrode 13e and an electrical circuit 59 connected across the two electrodes 13e and 58. The additional electrode 58 is a conventional solid metal electrode in this example but may in some cases be another optical fiber electrode. The circuit 29 of this embodiment includes an adjustable voltage source 61 connected in series with a current indicating ammeter 62 although in some cases the voltage source may be replaced with a current consuming component. Electrochemical cells which are used for electrolysis of solutions, for example, require an input of current while cells such as batteries or fuel cells are producers of current.

Except as hereinafter described, the optical fiber electrode 13e of this embodiment may be similar to the optical fiber 13b previously described with reference to FIG. 3. Thus, with reference again to FIG. 6, fiber 13e has a light transmissive core 17e with a thin coating 22e of silver or the like on the side surface and has a layer of opaque material 46e on the end surface 23e that is immersed in the liquid 12e. portions of the core 17e which extend out of liquid 12e have glass cladding 18e.

Optical fiber electrode 13e differs from the previously described optrodes in that it is provided with an electrical contact region 63 which is a layer of conductive metal substantially thicker than the metal coating 22e and which is in electrical contact with the coating. Layer 63 is in the form of an annular band around a portion of the fiber 13e in this particular embodiment. The contact layer 63 enables connection of a conductor 64 from circuit 59 to the optical fiber 13e by spot welding or other means. The thin metal coating 22e may then function as one of the electrodes of the cell 53.

Light source 14e directs monochromatic probe light to a dichroic mirror 27e which is angled to redirect such light into end 15e of optical fiber 13e through a focussing lens 33e. Raman signal detection means 16e of this embodiment includes a photomultiplier tube 34e having an output conductor 41e coupled to a current measuring and indicating device 42e. Raman signal light emitted from end 15e of the optical fiber electrode 13e passes through lens 33e and mirror 27e to an adjustable monochromator 37e of the type which enables signals of selected frequencies to be transmitted on to photomultiplier tube 34e through a focussing lens 38e.

The apparatus 11e of FIG. 6 operates essentially in the manner hereinbefore described with respect to initiating Raman signal emission from molecular species adsorbed on the surface of coating 22e and with respect to identifying and quantitating such species by frequency analysis of such signals. In particular, probe light propagating along fiber 13e produces an evanescent wave which induces the Raman signals from molecules adsorbed on the surface of the thin metal coating 22e. The Raman signals are returned by fiber 13e to photomultiplier tube 34e through lens 33e, mirror 27e, monochromator 37e and lens 38e. The monochromator 37e is adjusted to pass only Raman signal frequencies that are indicative of the molecular species that are to be detected. Ammeter 42 indicates the intensity of the particular Raman signal frequency that is being monitored at a particular time.

The optical fiber electrode 13e of FIG. 6 differs from the previously described optrodes in that it actively generates the species which it detects as it is a working electrode of an electrochemical cell. The products of the oxidation or reduction reactions which occur in such a cell adsorb on the surface of metal coating 22e enabling detection of the Raman spectra of such products. Data is obtained only from species at the electrode 13e surface rather than from other regions of the liquid 12e where reoxidation or re-reduction reactions may have changed the composition of the liquid. By selection of the frequency which is transmitted by monochromator 37e, the apparatus 11e may also be used to monitor fluorescence from species adsorbed on coating 22e. If, the probe light source 14e is pulsed, this enables measurement of the rates of diffusion of oxidation or reduction products away from the electrode 13e surface. The apparatus 11e may also be used to deliver light to electrochemically generated species at the coating 22e surface to induce and detect possible photochemical reactions of such species or, conversely, to photoactivate species prior to electrolysis.

While the invention has been described with respect to certain specific embodiments, many variations and modifications are possible and it is not intended to limit the invention except as defined in the following claims.

We claim:

1. In apparatus for detecting one or more molecular species in a liquid medium by surface enhanced Raman spectroscopy, the combination comprising:

at least one optical fiber having a light transmissive core and having a coating of metal on at least a portion thereof, said coating being sufficiently thin to transmit light, said metal being one which enhances emission of Raman signals by substances adsorbed on the surface of the coating when probe light is scattered by said substances, light source means for directing said probe light into said optical fiber, and detector means for detecting Raman signals in light which is emitted from said optical fiber.

2. The apparatus of claim 1 wherein said metal coating has a thickness in the range from about 10 Angstrom units to about 50 Angstrom units.

3. The apparatus of claim 1 wherein said light source means directs said probe light into a first end of said optical fiber and wherein said metal coating is on the opposite end of said fiber.

4. The apparatus of claim 3 wherein said metal coating is also present on at least a portion of the side surface of said core.

5. The apparatus of claim 4 wherein said metal coating is present on only a portion of said side surface of said core and wherein other portions of said side surface have a cladding of non-metallic light transmissive material that has a lower index of refraction than the material of said core.

6. The apparatus of claim 1 wherein said light source means directs said probe light into a first end of said optical fiber and wherein said apparatus further includes a layer of opaque material on the opposite end of said core, said metal coating being on at least a portion of the side surface of said core.

7. The apparatus of claim 6 wherein said metal coating extends along only a portion of said side surface of said core and wherein other portions of said side surface have a cladding of material of lower index of refraction than the material of said core.

8. The apparatus of claim 1 further including a layer of absorptive material covering said metal coating, said absorptive material being one which selectively absorbs a molecular species which is to be detected and which is non-absorptive of species which are not to be detected.

9. The apparatus of claim 1 wherein said metal is silver.

10. The apparatus of claim 1 wherein said metal is gold.

11. The apparatus of claim 1 wherein said metal is copper.

12. The apparatus of claim 1 wherein said light source means includes a monochromatic light source and a mirror positioned to direct light from said light source into a first end of said optical fiber, and wherein said detector means includes a photoelectric device of the type that produces an output signal that varies in accordance variations in the rate at which light is received by said device, means for directing light of predetermined frequency from said optical fiber to said photoelectric device and means for indicating values corresponding to the magnitude of said output signal of said photoelectric device.

13. The apparatus of claim 12 wherein said mirror is a dichroic mirror positioned to transmit light which is emitted from said first end of said optical fiber to said photoelectric device.

14. The apparatus of claim 12 wherein said means for directing light of predetermined frequency from said optical fiber to said photoelectric device includes a monochromator which is adjustable to selectively transmit any of a series of frequencies.

15. The apparatus of claim 1 further including an electrical contact layer of electrically conductive material disposed on a portion of said optical fiber, said contact layer being in electrical contact with the metal of said coating and being thicker than said coating.

16. The apparatus of claim 15 wherein said metal coating extends along the side surface of at least a portion of the side surface of said core and wherein said contact layer is an annular band of said electrically conductive metal encircling said optical fiber and overlying a portion of said metal coating.

17. Apparatus for detecting one or more substances in a fluid medium comprising:

an optical fiber having a light transmissive core with first and second opposite ends, a coating of metal on said core at least in the vicinity of said first end thereof, said coating being sufficiently thin to transmit light between said core and substances adsorbed on the surface of said coating, said metal being one which enhances Raman signal emission by said substances in response to probe light, a monochromatic probe light source, detector means for detecting specific frequencies of light, and means for directing probe light from said source into said second end of said optical fiber and for directing light which is emitted from said optical fiber to said detector means.

18. An optical fiber probe for use in detecting one or more constituents of a fluid, comprising an optical fiber having a light transmissive core and a metallic coating on at least a portion of said core, the metal of said coating being one which enhances emission of Raman signal light by substances adsorbed on the surface of the coating and the metal coating being sufficiently thin to transmit light between said core and said adsorbed substances.

19. The optical fiber probe of claim 18 wherein said metallic coating is disposed on an end surface of said core.

20. The optical fiber probe of claim 18 wherein said metallic coating extends along at least a portion of the side surface of said core and further including a layer of opaque material disposed on an end surface of said core.

21. The optical fiber probe of claim 18 wherein said metallic coating has a thickness in the range from about 10 Angstrom units to about 50 Angstrom units.

22. The optical fiber probe of claim 18 further including an electrical contact layer of electrically conductive metal overlying a portion of said metallic coating and being in electrical contact therewith, said layer being thicker than said metallic coating.

23. Apparatus for detecting one or more molecular species in the electrolytic liquid of an electrochemical cell while functioning as an electrode of said cell, comprising:

at least one optical fiber having a light transmissive core and having a metal coating extending along at least a portion of the side surface of said core, said coating being sufficiently thin to enable light transmission between said core and the outer surface of said coating and the metal of said coating being one which enhances emission of Raman signal frequencies by molecules adsorbed on said coating surface, means for directing probe light into an end of said optical fiber, means for detecting Raman signals which are emitted from said optical fiber, and a contact layer of electrically conductive material on a portion of said optical fiber, said layer being in contact with said metal coating and being thicker than said metal coating enabling connection of an electrical conductor of said cell to said thin metal coating.

* * * * *